Figure 1:
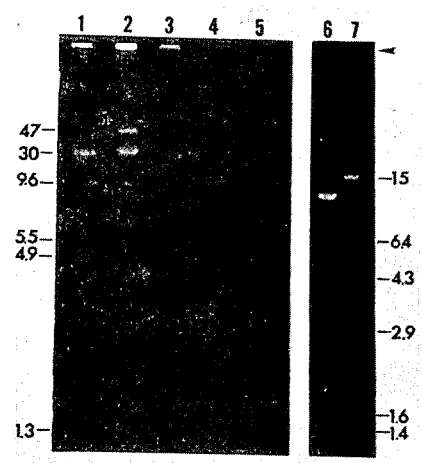

United States Patent [19]

Schnepf et al.

[11] Patent Number: 4,467,036

[45] Date of Patent: * Aug. 21, 1984

[54] BACILLUS THURINGIENSIS CRYSTAL PROTEIN IN ESCHERICHIA COLI

[75] Inventors: H. Ernest Schnepf; Helen R. Whiteley, both of Seattle, Wash.

[73] Assignee: The Board of Regents of the University of Washington, Seattle, Wash.

[*] Notice: The portion of the term of this patent subsequent to May 15, 2001 has been disclaimed.

[21] Appl. No.: 362,634

[22] Filed: Mar. 30, 1982

Related U.S. Application Data

[63] Continuation-in-part of Ser. No. 320,560, Nov. 12, 1981, abandoned, which is a continuation-in-part of Ser. No. 257,963, Apr. 27, 1981, Pat. No. 4,448,885.

[51] Int. Cl.$^3$ .................... C12N 1/00; C12N 15/00; C12N 1/20; C12P 21/00; A01N 63/00
[52] U.S. Cl. .................................. 435/317; 435/68; 435/172.3; 435/253; 424/93
[58] Field of Search ................ 435/172, 68, 317, 253, 435/70, 172.3; 424/93

[56] References Cited

PUBLICATIONS

Gonzalez et al: Plasmid 3, 92, (1980).
Rajalakshmi: Biol. Abstr. 72, 19676, (1980).
Lilley et al: J. Gen. Microbiol. 118, 1, (1980).
Delafield et al: J. Bacteriol. 96, 713, (1968).
Bolivar et al: Gene 2, 95, (1977).
Aronson, A. I., Angelo, N. and Holt, S. C., *J. Bacteriol.* 106:1016–1025, (1971).
Blair, D. G., Sherratt, D. J., Clewell, D. B., and Helinsky, D. R., *Proc. Nat. Acad. Sci., U.S.A.*, 69:2518–2522, (1972).
Bolivar, F., Rodriguez, R. L., Greene, P. J., Betlach, M. C., Heyneker, H. L., and Boyer, H. W., *Gene* 2:95–113, (1977).
Bradford, M., *Anal. Biochem.*, 72:248–254, (1976).
Cleveland, D. W., Fischer, S. G., Kirschner, N. W., and Laemmli, U. L., *J. Biol. Chem.*, 252(3):1102–1106, (1977).
Erlich, H. A., Cohen, S. N., and McDevitt, H. O., *Cell*, 13:681–689, (1978).
Henning, U., Schwartz, H. and Chen, R., *Anal. Biochem.*, 97:153–157, (1979).
Lilley, M., Ruffell, R. N., and Somerville, H. J., *J. Gen. Microbiol.*, 118:1–11, (1980).
Maniatis, T., Hardison, R. C., Lacy, E., Lauer, J., O'Connell, C., Quon, D., Sim, G. K., and Efstratiadis, A., *Cell*, 15:697–701, (1978).
Maniatis, T., Jeffrey, A., and Kleid, D. G., *Proc. Nat. Acad. Sci., U.S.A.*, 72:1184–1188, (1975).
Meyers, J. A., Sanchez, D., Elwell, L. P., and Falkow, *J. Bacteriol.*, 127:1529–1537, (1976).
Renart, J., Reiser, J. and Stark, G. R., *Proc. Nat. Acad. Sci., U.S.A.*, 76:3116–3120, (1979).
Schnepf, H. E., and Whiteley, H. R., *Proc. Nat. Acad. Sci., U.S.A.*, 78:2893–2897, (1981).
Stahly, D. P., Dingman, D. W., Bulla, L. A., and Aronson, A. I., *Biochem. Biophys. Res. Comm.*, 84:581–588, (1978).
Thomashow, M. F., Nutter, R., Montoya, A. L., Gordon, M. P., and Nester, E. W., *Cell*, 19:729–739, (1980).
Wahl, G. M., Stern, M., and Stark, G. H., *Proc. Nat. Acad. Sci., U.S.A.*, 76:3683–3687, (1979).
White, F. F., and Nester, E. W., *J. Bacteriol.*, 141:1134–1141, (1981).

*Primary Examiner*—Thomas Wiseman
*Assistant Examiner*—James Martinell
*Attorney, Agent, or Firm*—Fitch, Even, Tabin & Flannery

[57] ABSTRACT

Expression of the crystal protein of *Bacillus thuringiensis* in *Escherichia coli* is described by use of plasmids containing heterologous DNA coding for the crystal protein. Genetically engineered bacterial host strains transformed by the plasmids of the invention express *Bacillus thuringiensis* crystal proteins without exhibiting the growth phase limitations characteristic of the natural bacterial host species.

3 Claims, 4 Drawing Figures

BACILLUS THURINGIENSIS CRYSTAL PROTEIN IN ESCHERICHIA COLI

The United States government has rights in this invention pursuant to a grant awarded by the Department of Health and Human Services.

This application is a continuation-in-part application of U.S. Ser. No. 320,560, filed Nov. 12, 1981, now abandoned which was a continuation-in-part application of U.S. Ser. No. 257,963, filed Apr. 27, 1981 now U.S. Pat. No. 4,448,885.

The disclosure describes plasmids that have been deposited with the American Type Culture Collection, Rockville, Md. 20852. Plasmid pES1 is carried in *Escherichia coli strain ES*12; the strain and plasmid have been assigned ATCC Number 31995. Plasmid pJWK20 is carried in *Escherichia coli* strain JWK1; the strain and plasmid have been assigned ATCC Number 31997. Plasmid pJWK18 is carried in *Escherichia coli* strain JWK11; the strain and plasmid have been assigned ATCC Number 31998. Applicants have directed that the bacterial strains and plasmids they carry be freely available to the general public upon the issuance of a United States Patent.

This invention relates generally to the production of substances for the control of insects injurious to certain plants. More particularly, the invention relates to an improved means for producing substances toxic to larvae of the tobacco hornworm *Manduca sexta* and related species.

As is well known, the crystal protein made by *Bacillus thuringiensis* is toxic to the larvae of a number of lepidopteran insects. Preparations containing crystals are used commercially as a highly selective biological insecticide. However, problems connected with the use of such insecticides, together with relatively high manufacturing costs, have made it difficult, in many cases, for such insecticides to compete effectively with other commercially available products.

The fact that *Bacillus thuringiensis* produces the crystal protein only during sporulation represents a significant disadvantage in connection with the manufacture and use of the crystals. Such a growth phase limitation, particularly in an industrial process, can result in inconvenience and excessive time requirements during manufacture. In fact, certain pressures resulting from growth phase limitations or other factors may even result in strains of *Bacillus thuringensis* losing their ability to produce the crystals. Such acrystalliferous strains do not have insecticidal activity.

It is an object of this invention to provide an improved means of manufacturing the *Bacillus thuringiensis* crystal protein.

Another object of the invention is to provide an improved means of manufacturing *Bacillus thuringiensis* crystal protein by transferring the DNA coding for the crystal protein of *Bacillus thuringiensis* to other microorganisms so that toxin production does not have any growth phase limitations.

Figure 2:
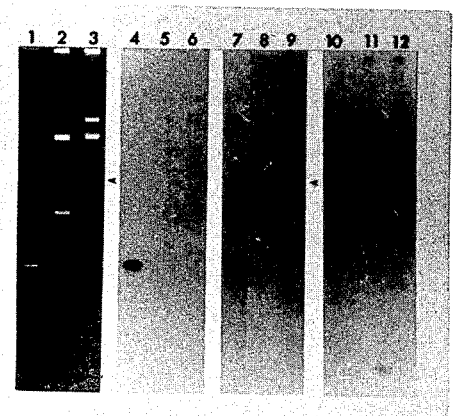
Figure 3:
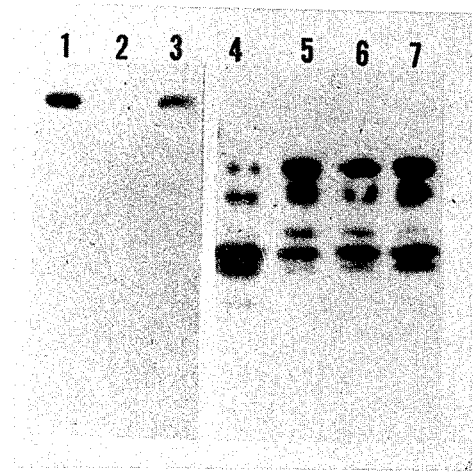
Figure 4:

Other objects of the invention will become apparent to those skilled in the art from the following description, taken in connection with the accompanying drawings wherein:

FIG. 1 is an agarose gel analysis of plasmid DNAs and marker DNA fragments comprising a photograph of 0.7% (lanes 1-5) and 0.35% (lanes 6 and 7) agarose slab gels stained with ethidium bromide;

FIG. 2 is a hybridization analysis of plasmid DNAs transferred to nitrocellulose comprising a photograph of a 0.7% ethidium bromide stained agarose gel (lanes 1-3) and autoradiograms of $^{32}P$ labeled plasmids (lanes 4-12); and FIG. 3 is a photograph showing a radioimmune assay of crystal protein and proteins produced by *Escherichia coli* bacterial strain ES12 before and after digestion with trypsin; and FIG. 4 is a photograph of an ethidium bromide stained gel showing plasmids detected in extracts of different strains of *Bacillus thuringiensis*.

Very generally, the invention discloses plasmids that are capable of replication in a bacterial host species and that contain expressible heterologous DNA encoding for the crystal protein of *Bacillus thuringiensis*. The plasmids further include an expression mechanism for the heterologous DNA which is recognized by the host species' system but does not exhibit any substantial growth phase limitations in the bacterial host species. In another form, the invention comprises genetically engineered bacterial strains transformed by such plasmids.

*Escherichia coli* bacterial strains genetically engineered to contain the recombinant plasmids of the present invention can be transformed to express *Bacillus thuringiensis* crystal protein. The protein produced by these genetically engineered strains is toxic to the larvae of a number of lepidopteran insects. Preparations containing these crystals can be used as a highly selective biological insecticide.

In accordance with a preferred form of the invention, novel hybrid recombinant plasmids are created when the known cloning vector plasmid pBR322, Bolivar et al, Gene 2:95-113 (1977), is combined with plasmid fragments obtained from plasmids harbored by strains of *Bacillus thuringiensis*. The "large plasmid fraction" is especially preferred. This "large plasmid fraction" includes fragments having a size greater than about 10 megadaltons. The plasmids harbored by strains of *Bacillus thuringiensis* are believed to be responsible for the production of the crystal protein in *Bacillus thuringiensis*. The *Bacillus thuringiensis* plasmid fragments used to construct the recombinant crystal protein coding plasmids of the present invention can be derived from a variety of *Bacillus thuringiensis* strains, many of which are publically available. For example, *Bacillus thuringiensis* subspecies *kurstaki* strain HD-1 is available from the Agricultural Research Culture Collection (NRRL) in Peoria, Ill., U.S.A. It has been awarded NRRL Number B-3792. *Bacillus thuringiensis* subspecies *kurstaki* strain HD-73 is also available from the Agricultural Research Culture Collection. It has been awarded NRRL Number B-4488. Examples are included in the specification to illustrate the use of several *Bacillus thuringiensis* strains. These other *Bacillus thuringiensis* strains are available either from Howard T. Dulmage, Cotton Insects Laboratory, United States Department of Agriculture Laboratory, P.O. Box 1033, Brownsville, Tex. 78520 or from the Bacillus Genetic Stock Center, Ohio State University, Department of Microbiology, 484 West 12th Avenue, Columbus, Ohio 43210. Such examples are included for illustrative purposes only and are not intended to limit the scope of the invention to use of fragments derived from such strains.

EXAMPLE I

Use of *Bacillus thuringiensis* subspecies *kurstaki* strain HD-1-Dipel plasmid DNA fragments in the construction of the recombinant plasmids of the present invention.

Crystal-producing strains of *Bacillus thuringiensis* vary in the number and sizes of the plasmids they contain. Plasmids obtained from *Bacillus thuringiensis* subspecies *kurstaki* strain HD-1-Dipel range in molecular mass from approximately 47 to 1.32 megadaltons as shown in lane 1 of FIG. 1, which shows the total plasmid complement normally obtained from this strain. Larger plasmids are present in this strain but were not readily detected as closed circular forms under the conditions of growth used in this study. However, plasmid fractions isolated from *Bacillus thuringiensis* contained small amounts of the linearized forms of these large plasmids. Two plasmid fractions were obtained from the *Bacillus thuringiensis* subspecies *kurstaki* HD-1-Dipel strain, as shown in lanes 2 and 3 of FIG. 1. One fraction, shown in lane 2, contained the 47, 32 and 30 megadalton plasmids as well as trace amounts of linearized forms of the very large plasmids of *Bacillus thuringiensis* (molecular weight $\times 10^6$ shown on left). The second fraction contained smaller plasmids of 4, 9, 5.2, 5.5 and 9.6 megadaltons, as shown in lane 3.

A preferred hybrid recombinant plasmid of the invention, designated pES1 (ATCC Number 31995), is shown in lane 4 of FIG. 1 in which the gel analysis of the plasmid may be compared with pBR322, shown in lane 5. After digestion by an enzyme which cuts the plasmid once, the linearized plasmid had a mobility corresponding to ca. $11 \times 10^6$ $M_r$ when compared to Hind III digested lambda DNA (shown in lanes 6 and 7 of FIG. 1). Molecular weights ($\times 10^{-6}$) on the right of the Figure refer to the Hind III digest of lambda DNA. The arrow on the right in FIG. 1 marks the origin for lanes 6 and 7.

In constructing hybrid recombinant plasmids, such as pES1 (ATCC Number 31995) according to the invention, the following detailed procedure were followed. These procedures are also outlined in Schnepf and Whiteley, *Proc. Nat. Acad. Sci.* USA, 78:2893-2897 (1981). They are given only by way of example and are not intended to limit the scope of the claims herein.

The two separated plasmid fractions, designated as "large" and "small", obtained from *Bacillus thuringiensis* subspecies *kurstaki* strain HD-1-Dipel were digested with varying dilutions of Sau3A1. This was monitored by agarose gel electrophoresis. To generate a source of inserts, the "large plasmid fraction" was digested with the minimum amount of enzyme needed to convert all the closed covalent circular molecules to the linear form. Restriction endonucleases Sal I, Hind III, BamH 1 and Sau3A1 were used as recommended by the manufacturer (New England Biolabs). This resulted in fragments with an average size greater than 10 megadaltons. For the "small plasmid fraction", an amount of Sau3A1 was used which left some closed covalent circular molecules, but produced few linear fragments under $2 \times 10^6$ $M_r$ in size.

Each fraction was then ligated to pBR322 that had been opened by digestion with the restriction enzyme Bam H1. Plasmid pBR322 was isolated from *Escherichia coli* strain HB101 (pBR322) as outlined by Blair et al *Proc. Nat. Acad. Sci.*, USA, 69:2518-2522 (1972). DNA fragments (3 µg of *Bacillus thuringiensis* plasmid DNA and 0.15 µg of pBR322 DNA in a volume of 10 µl) were ligated as described for cohesive ends by Maniatis et al in Cell 15:667-701 (1978).

Recombinants were then screened and selected. Staphylococcus Protein A (Pharmacia) was labeled with $^{125}$I (Amersham) using chloramine T as described by Erlich et al, Cell 13:681-689 (1978). The DNA polymerase I-catalysed fill-in reaction described by Maniatis et al *Proc. Nat. Acad. Sci.*, USA, 72:1184-1188 (1975) was used to label DNA fragments of Sau3A1 digests with [a-$^{32}$P]dCTP (Amersham).

Plasmids were obtained from *Bacillus thuringiensis* subspecies *kurstaki* strain HD-1-Dipel, kindly provided by Dr. Lee A. Bulla, Jr., according to the method for plasmid screening of White and Nester, *J. Bacteriol.* 141:1134-1141 (1980). All plasmid preparations were additionally purified by centrifugation in cesium chloride-ethidium bromide gradients. Samples (100 µg DNA per gradient) for cloning experiments were fractionated by centrifugation through 5-25% sucrose gradients for 2.5 hours at 35,000 RPM in an International B-60 centrifuge using the SB-283 rotor. Electrophoresis in agarose gels was used to analyze plasmid DNAs as described by Meyers et al, *J. Bacteriol.* 127:1529-1537 (1976). Fragments of the plasmids were produced by digestion of DNA with restriction enzymes as is known in the art. Hybridization to plasmid DNAs was performed after partial depurination as described by Wahl et al, *Proc. Nat. Acad. Sci.*, USA, 76:3683-3687 (1979) and transfer of DNA from gels to nitrocellulose was done as described by Thomashow et al Cell 19:729-739 (1980).

The recombinant plasmids thus produced were then transformed into *Escherichia coli*. Transformation was carried out as described by known procedures and transformants were selected on media containing 100 µg/ml ampicillin. Since cloning was performed by insertion of messenger DNA into the BamH 1 site of pBR322, which is located in a gene coding for tetracycline resistance, ampicillin resistant transformants were screened for sensitivity to tetracycline (25 µg/ml). Colonies resistant to ampicillin but sensitive to tetracycline were presumed to contain inserts.

Those transformed colonies presumed to carry *Bacillus thuringiensis* DNA inserts were then screened for the production of crystal protein antigen using antibodies and $^{125}$I-Protein A. To prepare antibodies to the crystals, the crystals were first purified from sporulated cultures of *Bacillus thuringiensis* grown in modified G medium, Aronson et al, *J. Bacteriol.* 106:1016-1025 (1971), by four successive centrifugations in Renografin (Squibb) gradients. Contamination with spores was estimated at less than 0.1% by phase microscopy. Solubilized crystals were electrophoresed on preparative 10% polyacrylamide slab gels containing NaDodSo4, and the portion of the gel containing the major crystal protein polypeptide was sliced from the gel, crushed, mixed with an equal amount of Freund's Complete Adjuvant and used to immunize rabbits. The immunoglobulin G fraction was purified from the serum of the immunized rabbits by precipitation with ammonium sulfate and chromatography on DEAE cellulose and analyzed by Ouchterlony immunodiffusion, as is known in the art.

To screen by detection of antigens, colonies were first transferred from agar plates to filter paper and denatured with phenol-chloroform-heptane and chloroform-methanol as described by Henning et al, *Anal. Biochem.* 97:153-157 (1979). The filters were soaked in 1% bovine serum albumen (Sigma, fraction V) and incubated with antibody and $^{125}$I-Protein A as described by Renart et al, *Proc. Nat. Acad. Sci.*, USA, 76:3116–3120, (1979). Colonies containing material capable of reacting with the crystal protein antibodies were detected by autoradiography. The concentrations of antibody ($10^{-3}$ to $10^{-4}$ dilution) and $^{125}$I-Protein A (0.2 to $1\times10^6$ cpm) were varied to obtain conditions permitting the detection of 5 ng crystal protein in 1 µl spotted on a filter while colonies of *Escherichia coli* strain HB101 (pBR322) were either unreactive or appeared light against a grey background. Protein samples were electrophoresed on 10% NaDodSO$_4$/polyacrylamide slab gels, transferred electrophoretically to nitrocellulose, and incubated with antibody ($5\times10^{-3}$ dilution) and $^{125}$I-Protein A ($6\times10^5$ cmp) in accordance with known procedures. The reaction of transferred peptides with antibody and $^{125}$I-Protein A was detected by radioautography.

Cells grown for 16 hours in L broth containing 100 µg/ml ampicillin were harvested by centrifugation, suspended in 0.1M Tris buffer at pH 7.0, 1 mM EDTA, 200 µg/ml phenylmethylsulfonyl fluoride and disrupted by sonication. Insoluble material, obtained by centrifugation of the sonicates at 100,000×g for 30 minutes, was thoroughly suspended in 4M urea, 0.285M 2-mercaptoethanol, 0.05M NaHCO$_3$, pH 9.5, and dialysed against 0.05M Tris buffer pH 7.4 for insect toxicity assays or for electrophoretic analysis. For proteolysis with subtilisin or trypsin, the samples were prepared as above substituting 0.05M cyclohexylaminoethane sulfonic acid (CHES), pH 10.0, 0.285M 2-mercaptoethanol for pH 9.5 urea buffer; final dialysis was against 0.01M CHES buffer, pH 10.0. For trypsin digestion, 0.01M CHES was used as the buffer and digestion was carried out at room temperature during dialysis against that buffer; digestion with subtilisin was performed according to Cleveland et al, *J. Biol. Chem.* 252:1102–1106 (1977). The reactions were stopped by boiling the samples in electrophoresis sample buffer and polypeptides capable of reacting with antibody to the crystal protein were detected using $^{125}$I-Protein A and radioautography as described above. Protein concentrations were determined according to Bradford, *Anal. Biochem.* 72:248–254 (1976).

The recombinant plasmid pES1 (ATCC Number 31995) consists of the plasmid vector pBR322 and DNA homologous to the 30, 32 and 47 megadalton plasmids, as well as DNA homologous to linearized forms of the very large plasmids of *Bacillus thuringiensis*. One explanation for this result is that several Sau3A1 partial digest fragments from each of the large *Bacillus thuringiensis* plasmids, were ligated together; this heteromultimer could then have been ligated into the vector. Another possibility is that the apparent hybridization to the 47 megadalton plasmid as shown in FIG. 2, is acutally a trailing artifact from the 30 or 32 megadalton plasmids.

EXAMPLE II

Evidence that *Escherichia coli* transformed by recombinant hybrid plasmids of the present invention produce *Bacillus thuringiensis* crystal protein.

The recombinant hybrid plasmids of the present invention can be used to transform *Escherichia coli* cells. These transformed cells produce *Bacillus thuringiensis* crystal protein. Such transformation is possible because the recombinant hybrid plasmids of the present invention contain both vector DNA and DNA from *Bacillus thuringiensis* plasmids that codes for the crystal protein. Plasmid pES1 (ATCC Number 31995) was used to demonstrate this.

As illustrated in FIG. 2, plasmid pES1 carried in *Escherichia coli* strain ES12 (ATCC Number 31995) contains substantial homology with DNA from the plasmid pBR322 as well as DNA homologous to the 30, 32 and 47 megadalton plasmids as well as DNA homologous to linearized forms of the very large plasmids of *Bacillus thuringiensis*. In FIG. 2, lanes 1–3 show a photograph of a 0.7% ethidium bromide-stained agarose gel: Lane 1 shows BamH 1 digested pBR322 DNA; lane 2 shows total plasmid complement of *Bacillus thuringiensis* and lane 3 shows the "large plasmid fraction" from *Bacillus thuringiensis*. Lanes 4–6 show an autoradiogram of $^{32}$P-labeled pBR322 DNA hybridized with: BamH 1 digested pBR322 DNA, as shown in lane 4; total plasmid complement, as shown in lane 5; and the "large plasmid fraction" from *Bacillus thuringiensis*, as shown in lane 6. Lanes 7–9 show an autoradiogram of $^{32}$P-labeled pES1 (ATCC Number 31995) DNA hybridized with: BamH 1 digested pBR322, as shown in lane 7; total plasmid complement, as shown in lane 8; and "the large plasmid fraction" from *Bacillus thuringiensis*, as shown in lane 9. Lanes 1–12 show an autoradiogram of $^{32}$P-labeled total *Bacillus thuringiensis* plasmid DNA hybridized with: BamH 1 digested pBR322 DNA as shown in lane 10; total plasmid complement, as shown in lane 11; and the "large plasmid fraction" from *Bacillus thuringiensis*, as shown in lane 12. The arrows in this Figure show the position of the linearized fragments and the hybridization of the probe to such fragments.

FIG. 3 presents a radioimmune assay of crystal protein produced by transformed *Escherichia coli* strain ES12 before and after digestion with trypsin. Autoradiograms of a solid-phase radioimmune assay for polypeptides are shown in lanes 1–3 of FIG. 3. These fragments react with anti-crystal antibody following $NaDodSO_4$/polyacrylamide gel electrophoresis. Lane 1 shows 1 μg *Bacillus thuringiensis* crystal protein. Lane 2 shows 100 μg *Escherichia coli* strain HB101 (pBR322) protein extract. Lane 3 shows 100 μg *Eschichia coli* strain ES12 protein extract. Lane 4 is derived from dissolved *Bacillus thuringiensis* crystals reacted with 5% (wt/wt) trypsin at pH 10 for 3 hours at room temperature. Lanes 5–7 show the ES12 extract reacted with: 2% (wt/wt) trypsin, as shown in lane 5; 4% (wt/wt) trypsin, as shown in lane 6; and 6% (wt/wt) trypsin at pH 10 for 3 hours at room temperature, as shown in lane 7.

Lanes 1–3 of FIG. 3 show that the antigen made by strain ES12, which reacted with crystal protein antibodies, had the same electrophoretic mobility as the *Bacillus thuringiensis* crystal protein. Dissolved *Bacillus thuringiensis* crystals and cell extracts of strain HB101 (pBR322) and strain ES12 were electrophoresed on a $NaDodSO_4$/polyacrylamide gel and reacted with anti-crystal antibody and $^{125}$I-Protein A after transfer to nitrocellulose. The ES12 extract, shown in lane 3 of FIG. 3, contained a polypeptide antigen having the same (or very similar) electrophoretic mobility as the dissolved *Bacillus thuringiensis* crystals shown in lane 1 of FIG. 3. This polypeptide antigen was missing from a similar extract of HB101 (pBR322), as shown in lane 2 of FIG. 3, and was not detected when pre-immune serum was substituted for anti-crystal antibody, or when $^{125}$I-Protein A was used without prior antibody treatment (data not shown).

Comparison of the bands shown in FIG. 3 (1 μg crystal protein in lane 1) with the total amount of protein applied to lane 3 (100 μg) indicates that the crystal protein antigen accounts for a small amount of the protein (1% or less) in ES12. When the radioimmune detection of polypeptide was used to monitor the fractionation of ES12 extracts it was found that a reducing agent plus a denaturant or an alkali pH was required to solubilize the crystal protein antigen. These conditions are also required to solubilize *Bacillus thuringiensis* crystals.

It has been reported by Lilley et al, *J. Gen. Microbiol.* 118:1–11 (1980) that the crystal protein can be digested by a number of proteases at pH 10 to produce primarily a single polypeptide. Lanes 4–7 of FIG. 3 show the results of an experiment where dissolved *Bacillus thuringiensis* crystals and an eluate from the particulate fraction of ES12 were subjected to partial digestion at pH 10 with the indicated amounts of trypsin. As seen in lanes 5, 6, and 7 of FIG. 3, digestion of the ES12 extract with increasing amounts of trypsin yielded a pattern, as shown in lane 7 of FIG. 3, which was similar to the pattern produced by trypsin digestion of the crystal protein of *Bacillus thuringiensis*, as shown in lane 4 of FIG. 3. Qualitatively the patterns of the bands generated from the two preparations were similar. The quantitative, and minor qualitative, differences may reflect a less efficient digestion of the crystal protein antigen in ES12 extracts due to the presence of numerous other polypeptide species.

The larger number of polypeptides produced by trypsin digestion of the crystal protein in these experiments as opposed to the number reported by Lilley et al, supra, may be due to differences in the conditions of trypsin treatment. Similar experiments using subtilisin also showed agreement in the electrophoretic mobilities of the bands produced from the crystal protein of *Bacillus thuringiensis* was obtained by assaying for insect toxicity. Extracts of particulate fractions obtained from *Escherichia coli* strain HB101 (pBR322) and ES12 were mixed with feed meal supplied to neonate caterpillars of the tobacco hornworm *Manduca sexta*. Neonate larvae of the *Manduca sexta* were supplied by Drs. J. Truman and L. Riddiford, Department of Zoology, University of Washington. Extracts were prepared as described above from 8 liters of the appropriate *Escherichia coli* strain 6–8 mls of extract were mixed with 50 ml of molten agar-based diet and quickly poured to give a shallow layer. Strips of the solidified diet were placed in glass vials (3–4 ml/vial) with one neonate larva for 10 days at room temperature.

The results indicated that the extracts of the genetically engineered recombinant strain were toxic to caterpillars. The 15 larvae exposed to the ES12 extracts did not complete the first instar before death. An equivalent amount of extract from control strain, *Escherichia coli* HB101 (pBR322), had no noticeable effect on the growth and development of 15 larvae through at least the third instar when compared to larvae grown on feed meal without any extract added. Identical results were obtained when this experiment was repeated with another set of *Escherichio coli* extracts. The minimal amount of extract of ES12 required to kill the caterpillar larvae has not yet been determined. Assuming that the crystal protein antigen in the ES12 extracts was 0.5–1% of the total protein, then the feed meal prepared with the extract from ES12 contained 12–25 μg crystal protein per ml whereas a concentration of 2 μg/ml of pure crystal protein is sufficient to achieve 100% killing of the larvae.

The resulting transformed strain of *Escherichia coli*, ES12, carries a recombinant plasmid and produces a protein antigen that reacts with antibodies specific for the crystal protein of *Bacillus thuringiensis*. This is confirmed by the above described tests wherein the recombinant plasmid isolated from this strain, pES1 (ATCC Number 31995) simultaneously transforms cultures of *Escherichia coli* strain HB101 to both ampicillin resistance and the production of the crystal protein antigen, whereas the plasmid vector pBR322 transforms HB101 to ampicillin and tetracycline resistance but no crystal antigen can be detected. Test results indicate that the DNA insert of the recombinant plasmid pES1 (ATCC Number 31995) encodes the ability to make a polypeptide possessing properties similar to those of the crystal protein of *Bacillus thuringiensis.* In fact, the results strongly suggest that the DNA insert of pES1 (ATCC Number 31995) encodes the gene for the crystal protein of *Bacillus thuringiensis* and that this gene is expressed in a biologically active form in *Escherichia coli.* Preparations made from this new genetically engineered strain, ES12, may therefore be used as an insecticide for appropriate cases.

EXAMPLE III

Use of *Bacillus thuringiensis* subspecies *kurstaki* strain HD-73 (NRRL B-4488) plasmid DNA fragments in the construction of the recombinant hybrid plasmids of the present invention.

*Bacillus thuringiensis* subspecies *kurstaki* strain (HD-73 contains fewer so-called large plasmids than do some of the other *Bacillus thuringiensis* strains. However, as this example illustrates, this strain can be used to generate the DNA fragments utilized in constructing the recombinant hybrid plasmids of the present invention. The "large plasmid fraction" from *Bacillus thuringiensis* subspecies *kurstaki* strain HD-73 was obtained by sucrose gradient centrifugation in the same way as the "large plasmid fraction" from *Bacillus thuringiensis* subspecies *kurstaki* strain HD-1-Dipel described in Example I. Digestion of this fraction with restriction enzyme Bgl II yielded approximately six fragments, one of which hybridized with a Pvu II-C DNA probe obtained from pES1 (ATCC Number 31995). The probe is discussed more fully in Example IV. The "large plasmid fraction" was digested with Bgl II, ligated to BamH I-digested pBR322 and transformed into *Escherichia coli.* Colonies which were ampicillin-resistant and tetracycline-sensitive were screened for hybridization with the Pvu II-C DNA probe and for their ability to synthesize the crystal protein antigen. James W. Kronstad isolated a strain, designated JWK1, having a plasmid, pJWK20 (ATCC Number 31997), whose linearized mass is approximately 13.5 megadaltons. The results of preliminary analyses using Bgl II, Sal I, and Hind III digestion of pJWK20 and the "large plasmid fraction" from strain HD-73 suggest that pJWK20 has a single insert of approximately 10.9 megadaltons derived from the 45 megadalton plasmid of *Bacillus thuringiensis* subspecies *kurstaki* strain HD-73.

Extracts of genetically engineered strain JWK1 were found to contain a polypeptide of approximately 130,000 $M_r$ which reacted with the antibody to the crystal protein from strain HD-1-Dipel. The mobility of this peptide matched that of the crystal protein from strain HD-1-Dipel. Tests for insect toxicity showed that feed meal supplemented with extracts of transformed *E. coli* strain JWK1 where lethal for larvae of the tobacco hornworm. The onset of toxic symptoms was similar to that observed for larvae fed with meal containing solubilized crystal protein. As in previously described toxicity tests, meal containing extracts of *Escherichia coli* (pBR322) did not retard the growth of the larvae. Thus it can be seen that genetically engineered *Escherichia coli* strain JWK1 produces a protein which is similar in size, antigenicity and biological activities to the crystal protein of *Bacillus thuringiensis* strain HD-1-Dipel.

EXAMPLE IV

Survey of *Bacillus thuringiensis* strains for plasmid content and the ability of these plasmids to hybridize with a probe from pES1 (ATCC Number 31995).

Restriction enzyme analysis of transposon Tn5 inserts into pES1 (data not shown) indicates that a major portion of the presumed crystal protein gene is contained within two Pvu II cleavage sites on the *Bacillus thuringiensis* plasmids. The cleavage sites define a Pvu II-C DNA fragment that can be used as a probe to analyze plasmid profiles of the various strains of *Bacillus thuringiensis* to determine which plasmids contain the gene. The Pvu II-C probe fragment was purified by sucrose gradient sedementation. The DNA fragments were labeled with alpha-$^{32}$-P-dCTP using either the DNA polymerase-catalyzed fill-in reaction described by Maniatias et al, Cell 15:667–701 (1978), or by nick translation, described by Maniatias et al, *Proc. Nat. Acad. Sci., USA* 72:1184–1188 (1975). The probe was then hybridized to plasmids from various *Bacillus thuringiensis* strains after electrophoresis and transfer to nitrocellulose. At the time of filing, about twenty crystal-producing strains of *Bacillus thuringiensis* had been examined for plasmid content and the ability of these plasmids to hybridize with the Pvu II-C probe fragment from pES1 (ATCC Number 31995). An example of one of the gels run as part of this survey is shown in FIG. 4. The photograph is of an ethidium bromide stained gel that shows plasmids detected in extracts of various *Bacillus thuringiensis* strains. Lane a is subspecies *tolworthii;* lane b is subspecies *darmstadiensis;* lane c is subspecies *sotto;* lanes d–g are subspecies *thuringiensis* strains F-10, HD-290, HD-120, and HD-2 respectively; lanes h–j are subspecies *kurstaki* strains HD-244, HD-73 and HD-1, respectively. The numbers in the margin indicate plasmid size in megadaltons. Other gels were run (data not shown) with extracts from *Bacillus thuringiensis* subspecies *alesti* strain HD-4, subspecies *toumanoffi* strain F-9, subspecies *galleriae* strain HD-8, subspecies *wuhnanesis* strain F-6, and subspecies *morrisoni* strain F-5. The results of the electrophoresis shown in FIG. 4 demonstrated the presence of several plasmid bands in each one. Presumably, most of the bands consist of closed circular molecules although some bands may represent open circular forms. The strains varied greatly in the number and sizes of the plasmids they contained; however some bands of the same or similar mobilities were present in several strains. The inventors point out that the data presented in FIG. 4 represent the analysis of routine CsCl-purified plasmid preparations and that no attempts have been made to verify conditions of growth, plasmid extraction or electrophoresis in order to detect all possible plasmids or to duplicate electrophoretic conditions used by other investigators. In addition, the sizes have been roughly estimated by comparisons with the mobilities of plasmids whose contour lengths have been determined by electron microscopy by Stahley et al, *Biochem. Biophys. Res. Comm.,* 84:581–588 (1978).

The strains examined in the experiment shown in FIG. 4 differ in flagellar serotype and in their ability to cross-react with the antibody to the crystal protein of strain HD-1-Dipel. The serotype of the *kurstaki* strains is 3a, 3b; the *thuringiensis* strains are type 1; the subspecies *sotto* is type 4a, 4b; subspecies *darmstadiensis* is type 10 and subspecies *tolworthii* is type 9. See De Barjac and Bonnefoi, *C. R. Acad. Sci.,* 264:1811–1813 (1967). Fourteen of the twenty strains tested reacted with the antibody to the crystal protein of strain HD-1-Dipel and showed hybridization with Pvu II-C probe.

EXAMPLE V

Use of *Bacillus thuringiensis* subspecies *sotto* plasmid DNA fragments in the construction of the recombinant plasmids of the present invention.

The procedures used to clone the crystal protein gene from *Bacillus thuringiensis* subspecies *sotto* are essentially the same procedures used to clone the gene from *Bacillus thuringiensis* subspecies *kurstaki* strain HD-73. The procedures are outline in Example III.

The subspecies *sotto* was selected for cloning the crystal protein gene because it contains only two plasmids and belongs to a different serotype. To clone the gene, total plasmid DNA purified by centrifugation in a CsCl-ethidium bromide gradient was partially restricted with endonuclease Mbo I. The resulting fragments were ligated into the BamH I site of pBR322. After transformation into *Escherichia coli,* colonies were selected which were ampicillin-resistant and tetracycline-sensitive. These colonies were screened for their ability to hybridize with the Pvu II-C fragment and for their ability to produce the crystal protein. One recombinant strain, JWK 11 (isolated by James W. Kronstad), contained the plasmid pJWK18; the size of the inserted *Bacillus thuringiensis* plasmid DNA has not yet been determined accurately. Strain JWK 11 produces a 130,000 $M_r$ protein which cross-reacts with antisera prepared against the crystal protein isolated from *Bacillus thuringiensis kurstaki* HD-1-Dipel. Extracts of JWK 11 are toxic to larvae of *Manduca sexta*.

It may be seen therefore that, in accordance with the invention, crystal protein of *Bacillus thuringiensis* is produced by a host strain transformed with recombinant plasmids. In vivo, *Bacillus thuringiensis* only produces crystal protein during sporulation. An advantage of this invention is the absence of the necessity for the host to sporulate in order for expression of the crystal protein to occur. Expression of the genetic information in the plasmids of the invention is not limited to a specific growth phase in the host because the crystal protein is expressed in accordance with an expression mechanism that is recognized by the host species in all major growth phases. By removing growth phase restrictions, production of the toxin is now possible by continuous culture rather than batch culture. This can permit high rate, high productivity fermentations with a decrease in capital equipment requirements.

Various modifications of the invention in addition to those shown and described herein will become apparent to those skilled in the art from the foregoing description and accompanying drawings. Such modifications are intended to fall within the scope of the appended claims.

REFERENCES

1. Aronson, A. I., Angelo, N., and Holt, S. C., *J. Bacteriol.* 106:1016–1025 (1971).
2. Blair, D. G., Sherratt, D. J., Clewell, D. B., and Helinski, D. R., *Proc. Nat. Acad. Sci., USA*, 69:2518–2522 (1972).
3. Bolivar, F., Rodriguez, R. L., Greene, P. J., Betlach, M. C., Heyneker, H. L., and Boyer, H. W., *Gene* 2:95–113 (1977).
4. Bradford, M., *Anal. Biochem.* 72:248–254 (1976).
5. Cleveland, D. W., Fischer, S. G., Kirschner, M. W., and Laemmli, U. K., *J. Biol. Chem.* 252(3):1102–1106 (1977).
6. DeBarjac, H., and Bonnefoi, A., *C. R. Acad. Sci.* 264:1811–1813 (1967).
7. Erlich, H. A., Cohen, S. N., and McDevitt, H. O., Cell 13:681–689 (1978).
8. Henning, U., Schwarz, H., and Chen, R., *Anal. Biochem.* 97:153–157 (1979).
9. Lilley, M., Ruffell, R. N., and Somerville, H. J. *J. Gen. Microbiol.* 118:1–11 (1980).
10. Maniatis, T., Hardison, R. C., Lacy, E., Lauer, J., O'Connel, C., Quon, D., Sim, G. K., and Efstratiadis, A., Cell 15:667–701 (1978).
11. Maniatis, T., Jeffrey, A., and Kleid, D. G., *Proc. Nat. Acad. Sci., USA*, 72:1184–1188 (1975).
12. Meyers, J. A., Sanchez, D., Elwell, L. P., and Falkow, S., *J. Bacteriol.* 127:1529–1537 (1976).
13. Renart, J., Reiser, J., and Stark, G. R., *Proc. Nat. Acad. Sci., USA* 76:3116–3120 (1979).
14. Schnepf, H. E., and Whiteley, H. R., *Proc. Nat. Acad. Sci., USA* 78:2893–2897 (1981).
15. Stahly, D. P., Dingman, D. W., Bulla, L. A., and Aronson, A. I., *Biochem. Biophys. Res. Comm.* 84:581–588 (1978).
16. Thomashow, M. F., Nutter, R., Montoya, A. L., Gordon, M. P., and Nester, E. W., Cell 19:729–739 (1980).
17. Wahl, G. M., Stern, M., and Stark, G. H., *Proc. Nat. Acad. Sci., USA*, 76:3683–3687 (1979).
18. White, F. F., and Nester, E. W., *J. Bacteriol.* 141:1134–1141 (1981).

What is claimed is:

1. A hybrid recombinant plasmid capable of replication in an *Escherichia coli* bacterial host species, said plasmid containing expressible heterologous DNA coding for a polypeptide which has the immunological properties of the crystal protein of *Bacillus thuringiensis*, said plasmid further containing expressible heterologous DNA having a DNA portion derived from plasmids of *Bacillus thuringiensis* having a molecular mass greater than $10 \times 10^6$ $M_r$, said *Bacillus thuringiensis* derived DNA portion being identifiable with a Pvu II-C DNA fragment probe, said hybrid recombinant plasmid further comprising an expression mechanism for said expressible heterologous DNA which is recognized by the host species' system.

2. A hybrid recombinant plasmid capable of replication in an *Escherichia coli* bacterial host species, said plasmid containing expressible heterologous DNA coding for a polypeptide which has the immunological properties of the crystal protein of *Bacillus thuringiensis*, said plasmid further containing expressible heterologous DNA having a DNA portion derived from plasmids of *Bacillus thuringiensis* having a molecular mass greater than $10 \times 10^6$ $M_r$, said *Bacillus thuringiensis* derived DNA portion further being identifiable with a Pvu II-C DNA fragment probe, said *Bacillus thuringiensis* derived DNA portion further being selected from the group consisting of *Bacillus thuringiensis* subspecies *tolworthi*; *Bacillus thuringiensis* subspecies *darmstadiesis*; *Bacillus thuringiensis* subspecies *sotto*; *Bacillus thuringiensis* subspecies *thuringiensis*; *Bacillus thuringiensis* subspecies *thuringiensis*, strain HD-290; *Bacillus thuringiensis* subspecies *thuringiensis*, strain HD-120; *Bacillus thuringiensis* subspecies *thuringiensis*, strain HD-2; *Bacillus thuringiensis* subspecies *kurstaki*, strain HD-244; *Bacillus thuringiensis* subspecies *kurstaki*, strain HD-73; *Bacillus thuringiensis* subspecies *kurstaki*, strain HD-1; *Bacillus thuringiensis* subspecies *alesti*, strain HD-4; *Bacillus thuringiensis* subspecies *toumanoffi*, strain F-9; *Bacillus thuringiensis* subspecies *galleriae*, strain HD-8; *Bacillus thuringiensis* subspecies *wuhnanesis*, strain F-6 and *Bacillus thuringiensis* subspecies *morrisoni*, strain F-5; said hybrid recombinant plasmid further including an expression mechanism for said heterologous DNA which is recognized by the host species' system.

3. Hybrid recombinant plasmids having the *Bacillus thuringiensis* crystal protein coding characteristics of plasmids: pES1, as carried in *Escherichia coli* strain ES12, (ATCC Number 31995); pJWK20, as carried in *Escherichia coli* strain JWKI (ATCC Number 31997); and pJWK18, as carried in *Escherichia coli* strain JWKII, (ATCC Number 31998), and their progeny resulting from normal cell division of the parental bacterial cells or plasmids.

* * * * *